(12) United States Patent
Dittmer et al.

(10) Patent No.: US 10,881,866 B2
(45) Date of Patent: Jan. 5, 2021

(54) ELECTRICAL CONTACTING DEVICE FOR AN IMPLANTABLE MEDICAL DEVICE, AND METHOD FOR PRODUCTION

(71) Applicant: Heraeus Deutschland GmbH & Co. KG, Hanau (DE)

(72) Inventors: Robert Dittmer, Hanau (DE); Ulrich Hausch, Frankfurt am Main (DE); Ilias Nikolaidis, Frankfurt am Main (DE); Jens Trötzschel, Ronneburg (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 117 days.

(21) Appl. No.: 16/233,427

(22) Filed: Dec. 27, 2018

(65) Prior Publication Data

US 2019/0201699 A1 Jul. 4, 2019

(30) Foreign Application Priority Data

Jan. 2, 2018 (EP) .................................... 18150083

(51) Int. Cl.
*A61N 1/375* (2006.01)
*H05K 5/06* (2006.01)
*A61L 27/04* (2006.01)
*A61L 27/10* (2006.01)

(52) U.S. Cl.
CPC ......... *A61N 1/3752* (2013.01); *A61N 1/3754* (2013.01); *H05K 5/069* (2013.01); *A61L 27/04* (2013.01); *A61L 27/10* (2013.01)

(58) Field of Classification Search
CPC ....... A61L 27/04; A61L 27/10; A61N 1/3752; A61N 1/3754; H05K 5/069
See application file for complete search history.

(56) References Cited

U.S. PATENT DOCUMENTS 8,332,037 B2 12/2012 Imran
2012/0193125 A1 8/2012 Pavlovic et al.
(Continued)

FOREIGN PATENT DOCUMENTS

DE 102011009858 8/2012
EP 2837446 2/2015
WO 2013019458 2/2013

*Primary Examiner* — George Manuel
(74) *Attorney, Agent, or Firm* — Dicke, Billig & Czaja, PLLC

(57) ABSTRACT

One aspect relates to an electrical contacting device for a medical implantable device, including an electrically insulating base body with a first and a second surface. The base body includes a ceramics, an electrically conductive conducting element that extends from the first surface of the base body through the base body. The conducting element includes a cermet and is connected to the ceramics of the base body in firmly bonded manner through a sintered connection, a contact element including a metal. The contact element is connected to the conducting element in electrically conductive manner and can be connected to an electrically conductive structure. The contacting device includes an adhesion element. The adhesion element is connected to the contact element in firmly bonded manner and wherein the adhesion element includes an adhesion promoter in order to form a firmly bonded connection at least to the first surface of the base body.

23 Claims, 2 Drawing Sheets

(56) References Cited

U.S. PATENT DOCUMENTS

| | | | |
|---|---|---|---|
| 2013/0286566 A1* | 10/2013 | Tsuduki | H05K 5/0091 |
| | | | 361/679.01 |
| 2017/0296832 A1 | 10/2017 | Breyen et al. | |
| 2018/0050212 A1* | 2/2018 | Nikolaidis | A61L 27/10 |

* cited by examiner

ELECTRICAL CONTACTING DEVICE FOR AN IMPLANTABLE MEDICAL DEVICE, AND METHOD FOR PRODUCTION

CROSS-REFERENCE TO RELATED APPLICATION

This Utility patent application claims priority to Application No. EP 18150083.6, filed on Jan. 2, 2018, which is incorporated herein by reference.

TECHNICAL FIELD

One aspect relates to an electrical contacting device for a medical implantable device; a medical implantable device including a contacting device; a method for the production of an electrical contacting device; and the use of an electrical contacting device.

BACKGROUND

DE 10 2011 009 858 B4 describes an electrical bushing for use in a housing of a medical implantable device. The electrical bushing includes an electrically insulating base body made of ceramics and at least one electrical conducting element. The conducting element is operable to establish, through the base body, an electrically conductive connection between an internal space of the housing and an external space. The conducting element is hermetically insulated with respect to the base body and includes a cermet. In addition, the conducting element includes a connecting layer that includes a metal. The connecting layer is next to a wire-like structure, that is, the connecting layer is situated between the conducting element including the cermet and the wire-like structure. In this context, the connecting layer extends exclusively over the surface of the distal end of the conducting element, that is, the connecting layer does not contact the ceramic base body.

Known connecting layers, contact pads also, often consist of pure metal, for example, of a precious metal or a precious metal alloy. A strongly adhesive, firmly bonded connection between a pure metal layer and a ceramic body is difficult to attain in this context.

WO 2013/019458 A1 discloses hermetic bushings for implantable medical devices including an insulator made of a ceramic material, a conductor made of an electrically conductive material, and a contact pad. The contact pad can consist of multiple layers. The conductor includes a cermet and includes a widened region on at least one end. The contact pad is connected in firmly bonded manner to the widened region on the end of the conductor by means of a sintered connection. In this context, the widened region of the conductor is flush with the surface of the ceramic insulator. This is commonly realized in that a binding agent-containing cermet paste is introduced into the recess of a layer-like ceramic green body using a doctor blade. Subsequently, the laminate is burned, whereby the binding agent of the cermet paste combusts and a hermetically sealed, firmly bonded sintered connection between the cermet and the ceramic material is generated. The widened region of the conductor cannot be designed to have just any width or any extension since the expected shrinking of the compound material during the burning may lead to breakage of the laminate.

However, in many cases contact pads or generally contact elements are required that require a wide and/or complex spatial extension along the base body of a bushing or generally of a contacting device. This can be the case, for example, if the wire-like structure or generally the electrically conductive structure is not to be coupled on one of the ends or in the region of the ends of a conductor or generally of a conducting element, but in a region that is relatively distant from the end. The latter requires the contacting element used for connecting the conducting element and the electrically conductive structure to have a certain spatial extension.

US 2017/0296832 A1 discloses a method for producing a connection between a conducting element, including via, an electrical bushing, and a conducting wire, also lead, by means of a contact pad. The bushing includes a ceramic insulator, a platinum-including via, and a contact pad. The contact pad is electrically connected to the via and includes platinum. Moreover, the contact pad is connected to the insulator. As mentioned above, strongly adhesive connections between a pure metal and a ceramic insulator are difficult to realize, which can be a significant safety risk especially in the case of implantable devices.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
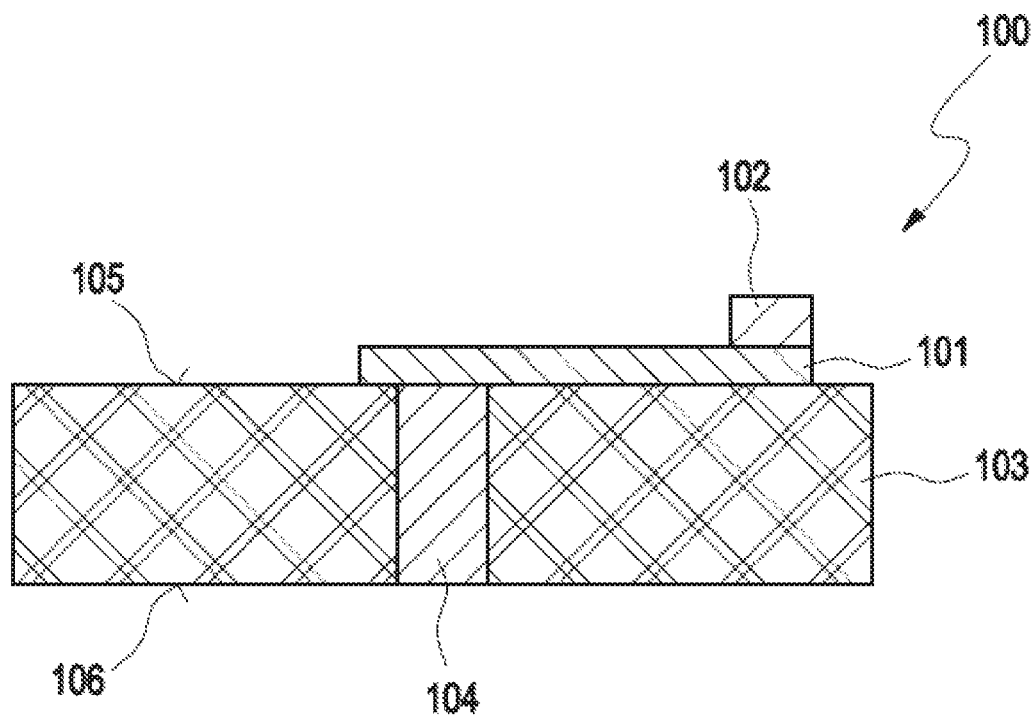
FIG. 1 illustrates a cross-sectional view of a contacting device according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

In general, it is an object of one embodiment to overcome the aforementioned disadvantages of the prior art.

It is another object of one embodiment to provide a contacting device that enables a strongly adhesive connection between a contact element and the ceramic part of the contacting device.

It is another object of one embodiment to provide a contacting device that allows the electrically conductive structure to be coupled via a contact element, which is electrically connected to the conducting element, independent of the spatial positioning of the conducting element.

The independent claims make a contribution to meeting, at least partially, at least one of the objects specified above. The dependent claims are embodiments that contribute to meeting, at least partially, at least one of the objects. In one embodiment, refinements of components of any inventive category, for example, of the electrical contacting device according to one embodiment, the catheter tip according to one embodiment and the method according to one embodiment, shall be used in the same manner for identically named or corresponding components of the corresponding other category according to the embodiments. The terms, "possessing", "comprising" or "including", etc., shall not exclude further elements, ingredients, etc., from possibly being contained. The indefinite article, "a", shall not exclude a plurality from being present.

For each embodiment, in which a component "comprises" a certain material, a corresponding embodiment is considered, as a matter of rule that consists of the material or essentially consists of the material. This shall apply both to the methods and to the products according to the embodiments.

In a one aspect, one embodiment proposes an electrical contacting device for a medical implantable device, including an electrically insulating base body having a first and a second surface, whereby the base body includes a ceramics, an electrically conductive conducting element;

that extends from the first surface of the base body at least in part through the base body, whereby the conducting element includes a cermet and is connected in firmly bonded manner to the ceramics of the base body by means of a sintered connection, a contact element including a metal, whereby the contact element is electrically connected to the conducting element and can be connected to an electrically conductive structure.

One embodiment provides the contacting device to include an adhesion element, whereby the adhesion element is connected to the contact element in firmly bonded manner, and whereby the adhesion element includes an adhesion promoter in order to establish a firmly bonded connection at least to the first surface of the base body.

In addition to the contact element enabling the connection to the electrically conductive structure, the contacting device according to one embodiment also includes an additional adhesion element. The adhesion element provides an adhesion promoter that provides a strongly adhesive, firmly bonded connection to at least the first surface of the ceramic base body. The adhesion element is connected to the contact element in firmly bonded manner, whereby the firmly bonded connection is made possible, for example, in that the adhesion element in one embodiment includes, aside from the adhesion promoter, a metal that enables a firmly bonded connection to the contact element, which also includes a metal. The firmly bonded connection of the adhesion element and the first surface of the ceramic base body and the contact element is in one embodiment to be a sintered connection.

The adhesion element in one embodiment includes a metal in order to enable an electrical connection between the contact element and the conducting element. In one embodiment, the adhesion element includes a precious metal or a precious metal alloy.

Therefore, one embodiment of the electrical contacting device is characterized in that the adhesion element includes a first layer, whereby the first layer includes a metal.

The adhesion element can include a layer that includes a metal for the formation of a firmly bonded connection to the contact element. In one embodiment, the adhesion element includes a precious metal or a precious metal alloy. For example, the adhesion element is arranged as a layer between the contact element and the first surface of the base body. In this context, the adhesion element covers, at least in part, the first end of the conducting element and a part of the ceramic surface of the base body that is designed as an insulator.

One embodiment of the electrical contacting device is characterized in that the adhesion element includes a first layer, whereby the first layer includes a metal and extends through a second layer to the conducting element, whereby the second layer includes a dielectric material and is connected in firmly bonded manner to at least the first layer and the first surface of the base body. The adhesion element can include at least two layers, whereby the first layer extends through the second layer and, in the process, contacts the conducting element. In this context, the first layer includes a metal in order to assure a strongly adhesive firmly bonded connection to the contact element as well as to the conducting element, which includes a cermet and therefore a metal. The second layer includes a dielectric material, whereby the material, as adhesion promoter, enables a firmly bonded connection to the first surface of the ceramic base body.

In one embodiment, the first layer and the second layer are made from different materials. In some embodiments, the first layer includes a metal, such as, for example, elemental platinum, whereas the second layer does not include elemental metal (that is, metal in an oxidation state of zero ($\pm 0$)).

The second layer is dielectric in some embodiments, that is, it is not electrically conductive, for example having an insulation resistance of at least $>1\times10E16$ Ohm*m. In some embodiments, the second layer consists essentially or fully of a dielectric material, for example of a ceramics of the type described in more detail hereinafter. In some embodiments, the second layer contains essentially no elemental metal (that is, metal in an oxidation state of zero ($\pm 0$)).

The first layer in one embodiment also includes an adhesion promoter that enables a strongly adhesive firmly bonded connection to the second layer. The second layer can extend exclusively along the first surface of the ceramic base body or, alternatively, can extend along the first surface of the ceramic base body and an end of the conducting element. In the former case, the second layer of the adhesion element contacts the contact element, the first layer of the adhesion element, and the conducting element. In the latter case, the second layer of the adhesion element contacts the contact element, the first layer of the adhesion element, but does not contact the conducting element.

For example, the second layer includes a hole, whereby the hole defines a recess through which the first layer extends to the conducting element. Accordingly, an electrical connection between the conducting element and the contact element can be established, if the second layer is electrically insulating. This is the case, for example, if the second layer essentially consists of a dielectric material, for example, a ceramics of the type described herein, and for example, includes no electrically conductive metal particles.

In some embodiments, the adhesion element is flush with the base body along an uninterrupted planar surface. In some embodiments, the adhesion element does not extend from the first surface of the base body into the base body, but is situated exclusively above the first surface of the base body.

In one embodiment of the electrical contacting device is characterized in that the adhesion promoter includes a ceramics, an amorphous glass, a recrystallizable glass or a combination of at least two thereof. A recrystallizable glass is preferred in one embodiment over an amorphous glass in this context.

In the spirit of one embodiment, a ceramics, an amorphous glass and/or a recrystallizable glass is a dielectric material In one embodiment, the adhesion promoter includes no glass or the adhesion promoter includes a ceramics exclusively. In this case, the first layer of the adhesion element does not include glass or the first layer of the adhesion element contains a ceramics exclusively as adhesion promoter. If the adhesion element includes two (or more) layers, then the first and the second layer do not include glass or the adhesion promoter of the first and of the second layer of the adhesion element includes no glass.

If the requirements concerning the biocompatibility, for example, concerning the biostability, of the contacting device are particularly high, for example if the contacting device is used for a medical implantable device, it is advantageous for the adhesion element to be free of glass in one embodiment.

In one embodiment of the electrical contacting device is characterized by the adhesion element including at least 10% by weight of the adhesion promoter, relative to the total weight of the adhesion element. In one embodiment, the adhesion element contains at least 25% by weight adhesion promoter or at least 35% by weight adhesion promoter.

In an embodiment, the adhesion element consists of particles of the adhesion promoter and of the metal that are sintered into a strongly adhesive layer after removal of the binding agent. According to another embodiment, the adhesion element therefore includes at least 40% by weight metal, in one embodiment at least 50% by weight, in one embodiment at least 75% by weight or 85% by weight or 90% by weight.

In one embodiment of the electrical contacting device is characterized in that the first layer includes a cermet.

The first layer can include a cermet if the adhesion element includes just a first layer or if the adhesion element includes a first layer and a second layer, whereby the first layer includes a metal and extends through a second layer to the conducting element.

In one embodiment of the electrical contacting device is characterized in that the cermet includes aluminum oxide and platinum.

In one embodiment, aluminum oxide is selected for the ceramic portion of the cermet and platinum is in one embodiment selected for the metal portion of the cermet.

In one embodiment of the electrical contacting device is characterized in that the amorphous glass includes at least 45% by weight silicon oxide ($SiO_2$).

In one embodiment of the electrical contacting device is characterized in that the recrystallizable glass includes at least 25% by weight aluminum oxide ($Al_2O_3$) and no more than 30% by weight silicon oxide ($SiO_2$).

The specified content relates, in each case, to the recrystallizable glass in the sintered or burned state. In one embodiment, the recrystallizable glass includes at least 40% by weight aluminum oxide, in one embodiment at least 45% by weight aluminum oxide, and in one embodiment no more than 60% by weight aluminum oxide. In one embodiment, the recrystallizable glass includes at least 10% by weight silicon oxide, in one embodiment at least 20% by weight silicon oxide, and in one embodiment at least 22% by weight silicon oxide.

In one embodiment of the electrical contacting device is characterized in that the adhesion element and the base body form an oxidic mixed crystal layer.

In one embodiment of the electrical contacting device is characterized in that the contact element includes a precious metal. In one embodiment precious metals include Pt, Au, Pd, and Ag or an alloy of at least two of the metals.

Contact elements made of Pd are preferred in one embodiment for wires that are used commonly in medical engineering and are made from the alloy MP35N®, which is a nickel-cobalt-chromium-molybdenum alloy.

One embodiment of the electrical contacting device is characterized in that the contact element is provided as a printed conductor.

This means that the contact element extends essentially two-dimensionally along the first surface of the base body, whereby the extension of the contact element in at least one direction is significantly larger than the diameter of the conducting element. The spatial dimension of the contact element can be at least five-times or ten-times or 100-times larger than the spatial dimension of the conducting element, for example, of the diameter of the conducting element. This enables an electrical contacting of the conducting element by the electrically conductive structure in a place that is situated relatively distant from an end of the conducting element.

In another embodiment, both the adhesion element and the contact element can be provided as printed conductor. It is also conceivable to provide the adhesion element as printed conductor and to have the contact element be applied suitably onto the adhesion element in one place, such that the spatial dimension of the contact element is significantly smaller than the spatial dimension of the adhesion element.

In one embodiment of the electrical contacting device is characterized in that the contact element is provided as a contact pad. This means that the spatial dimension of the contact element in at least one direction is not significantly larger than the spatial dimension of the conducting element. The spatial dimension of the contact element in one direction can be at most 4-times or 2-times or 1.5-times larger than the spatial dimension of the conducting element, for example, the diameter of the conducting element.

One embodiment of the electrical contacting device is characterized in that the contact element includes a metal produced by electrochemical deposition.

The adhesion element is electrically conducting, sentence at least one of the layers of the adhesion element includes a metal. This enables a galvanic or current-less the position of the contact element on the adhesion element. The advantage of this procedure is that the deposition of the contact element takes place exclusively in the region of the adhesion element, since only this surface, but not the first surface of the base body, is electrically conducting. As a result, the geometry of the contact element corresponds exactly to the geometry of the adhesion element. In addition, there is no need to use a mask-producing process.

One embodiment of the electrical contacting device is characterized in that the conducting element extends from the first surface of the base body through the base body to the second surface of the base body.

Since the conducting element extends from the first surface of the base body through the base body to the second surface of the base body, the contacting device can be used as a bushing in a medical device. In one embodiment, the first and second surfaces of the base body are parallel surfaces opposite from each other. In this context the conducting element can extend in a straight line, step-shaped or serpentine-like from the first surface to the second surface of the base body. The conducting element includes a first end in the region of the first surface of the base body and a second end in the region of the second surface of the base body.

One embodiment of the electrical contacting device is characterized in that the ceramics of the base body includes at least 90% by weight aluminum oxide ($Al_2O_3$), in one embodiment at least 99% by weight aluminum oxide, in one embodiment at least 99.9% by weight aluminum oxide.

In one embodiment, the contact element or the adhesion element are both combined have a layer thickness of 0.1 µm to 100 µm.

If the contact element is provided as contact pad, the diameter is typically in the range of 50 µm to 1000 µm. If the contact element is provided as printed conductor, the width of the printed conductor is typically in the range of 50 µm to 1000 µm.

A contribution to meeting at least one of the objects according to one embodiment is made by a medical implantable device, including a contacting device according to any one of the embodiments specified above.

For example, the electrical contacting device or the medical implantable device can be used in a cardiac pacemaker, a defibrillator, a neurostimulator, a cochlear implant, a glucose monitor or in an implantable infusion pump.

A contribution to meeting at least one of the objects of one embodiment is also made by a method for producing an electrical contacting device for a medical implantable device, whereby the process includes the following steps of:
  a. Providing an electrically insulating base body having a first and a second surface,
     whereby the base body includes a ceramics, and
     whereby the base body includes an electrically conductive conducting element
     that extends, at least in part, from the first surface of the base body through the base body,
     whereby the conducting element includes a cermet and is connected in firmly bonded manner to the ceramics of the base body through a sintered connection;
  b. generating an adhesion element including an adhesion promoter on the base body through a sintering step 1 from an adhesion element precursor while forming a firmly bonded connection at least between the adhesion element and the first surface of the base body;
  c. generating a contact element including a metal on the adhesion element through a sintering step 2 from a contact element precursor while forming an electrical connection between the contact element and the conducting element and a firmly bonded connection between the contact element and the adhesion element.

According to the method according to one embodiment, initially a base body including a ceramics is provided that includes an electrical conducting element that is surrounded by the base body and extends, at least in part, from the first side of the base body through the base body. In one embodiment, the conducting element extends fully from the first side of the base body through the base body to the second side, whereby the two sides of the base body are situated parallel and opposite from each other. The conducting element includes a cermet and is connected to the base body in firmly bonded and hermetically sealed manner.

Subsequently, an adhesion element is generated from an adhesion element precursor in a first sintering step (sintering step 1). The adhesion element includes an adhesion promoter. As a result of the sintering process, the adhesion element forms a firmly bonded connection at least to the base body, in the region of the first surface. In one embodiment, the adhesion element and the base body and the conducting element form a firmly bonded connection in the region of the first end of the conducting element.

In a subsequent step, a contact element is generated from a contact element precursor in a second sintering step (sintering step 2). The contact element includes a metal. Due to the sintering process, the contact element and the adhesion element form a firmly bonded connection. Since the adhesion element includes a metal in at least one layer that contacts the conducting element, sintering step 2 establishes an electrical connection between the contact element and the conducting element.

One embodiment of the method is characterized in that the adhesion element precursor includes at least one paste 1, whereby paste 1 includes at least a metal, an adhesion promoter, and a binding agent.

In one embodiment, paste 1 is used for application of the first layer of the adhesion element. The paste is first applied, then sintered or burned by means of which the first layer of the adhesion element is generated. In one embodiment, paste 1 is an electrically conductive paste such that the sintered first layer is also electrically conductive.

Accordingly, one embodiment of the method is characterized in that, in sintering step 1, paste 1 is being applied to the base body and sintered, whereby the adhesion element is formed while forming a firmly bonded connection to the conducting element and to the first surface of the base body.

In this context, paste 1 is in one embodiment contacted to the ceramic base body and to the surface of the conducting element.

One embodiment of the method is characterized in that the adhesion element precursor includes a paste 2, whereby paste 2 includes at least one adhesion promoter and a binding agent.

In one embodiment, paste 2 is used for application of the second layer of the adhesion element. The paste is first applied, then sintered or burned by means of which the second layer of the adhesion element is generated. In one embodiment, paste 2 is an electrically non-conductive or dielectric paste that does not include any electrically conductive metal particles. In some embodiments, a second layer of ceramics is formed by sintering paste 2.

One embodiment of the method is characterized in that the contact element precursor includes a paste 3, whereby paste 3 includes at least one metal and a binding agent.

For generating the contact element, it is preferred in one embodiment to use a paste 3 that includes at least one metal and a binding agent. After application of the paste onto the previously sintered adhesion element, paste 3 is being sintered or burned and the contact element is thus being generated. Alternatively, it is conceivable that both paste 1 and/or paste 2 and paste 3 are applied one after the other and are subsequently being sintered jointly, whereby the adhesion element and the contact element are generated in a single sintering step. Aside from the metal, paste 3 in one embodiment includes only components that are removed by heating to the corresponding sintering temperature, that is, are volatile at the sintering conditions, such that the contact element includes, exclusively or essentially, a metal after the sintering. Volatile components at sintering conditions include, for example, a binding agent, a solvent, a surfactant or an additive.

One embodiment of the method is characterized in that, in sintering step 1, paste 2 is initially applied appropriately to the base body and sintered such that at least a part of an exposed surface of the conducting element is not covered by paste 2, and subsequently paste 1 is applied onto the sintered paste 2 and sintered, whereby the adhesion element is formed while forming a firmly bonded connection to the conducting element and to the first surface of the base body.

In this case, a dielectric paste is initially applied onto the ceramic base body in appropriate manner such that a defined surface of the conducting element remains exposed such that the conducting element can be electrically contacted later on by means of paste 1, which includes electrically conductive metal particles. It is preferred in one embodiment to initially apply the dielectric paste 2 and sinter it. Subsequently, electrically conductive paste 1 is applied appropriately onto the sintered second layer such that paste 1 fills the region that has been left exposed by the second layer and contacts the exposed surface of the conducting element. Subsequently, paste 1 is sintered such that the first layer of the adhesion element is produced as well. As a result, a two-layered adhesion element was produced in sintering step 1.

In some embodiments, a mechanical processing of the surface of sintered paste 2 for smoothing of same is performed between the sintering of paste 2 and the sintering of paste 1. This can take place, for example, by means of grinding, polishing, etching or comparable procedures that are known and common in this field.

In another embodiment, paste 1 and paste 2 are being co-sintered.

Ceramics

A ceramics in the scope of one embodiment can be any ceramics that would be selected for use in one embodiment by a person skilled in the art. In one embodiment, the ceramics is selected from the group consisting of an oxide ceramics, a silicate ceramics, a non-oxide ceramics or a mixture of at least two thereof.

The oxide ceramics is preferably in one embodiment selected from the group consisting of a metal oxide, a metalloid oxide or a mixture thereof. The metal of the metal oxide can be selected from the group consisting of aluminum, beryllium, barium, calcium, magnesium, sodium, potassium, iron, zirconium, titanium or a mixture of at least two thereof. The metal oxide is in one embodiment selected from the group consisting of aluminum oxide ($Al_2O_3$), magnesium oxide (MgO), zirconium oxide ($ZrO_2$), yttrium oxide ($Y_2O_3$), aluminum titanate ($Al_2TiO_5$), a piezo-ceramics such as lead zirconate ($PbZrO_3$), lead titanate ($PbTiO_3$) as well as lead zirconate-titanate (PZT) or a mixture of at least two thereof. The metalloid of the metalloid oxide is in one embodiment selected from the group consisting of boron, silicon, arsenic, tellurium or a mixture of at least two thereof. In one embodiment oxide ceramics contains one selected from the group consisting of zirconium oxide-toughened aluminum oxide (ZTA—Zirconia Toughened Aluminum—$Al_2O_3/ZrO_2$), yttrium-toughened zirconium oxide (Y-TZP), barium(Zr, Ti) oxide, barium(Ce, Ti) oxide or a combination of at least two thereof.

The silicate ceramics is in one embodiment selected from the group consisting of a steatite ($Mg_3[Si_4O_{10}(OH)_2]$), cordierite ($(Mg, Fe^{2+})_2(Al_2Si)[Al_2Si_4O_{18}]$), mullite ($Al_2Al_{2+2x}Si_{2-2x}O_{10-x}$ where x=oxygen voids per elemental cell), feldspar ($(Ba, Ca, Na, K, NH_4)(Al, B, Si)_4O_8$) or a mixture of at least two thereof.

The non-oxide ceramics can be selected from the group consisting of a carbide, a nitride or a mixture thereof. The carbide can be selected from the group consisting of silicon carbide (SiC), boron carbide ($B_4C$), titanium carbide (TiC), tungsten carbide, cementite ($Fe_3C$). The nitride can be selected from the group consisting of silicon nitride ($Si_3N_4$), aluminum nitride (AlN), titanium nitride (TiN), silicon-aluminum-oxinitride (SIALON) or a mixture of at least two thereof. Sodium potassium niobate is in one embodiment non-oxide ceramics.

Amorphous Glass

According to one embodiment, an amorphous glass shall be understood to be a mixture of at least two different metal oxides and/or metalloid oxides that has an amorphous structure in the solid state at room temperature and remains in the amorphous state after heating to a certain sintering temperature and subsequent cooling. Accordingly, an amorphous glass does not form crystals or crystalline areas after heating beyond the glass transition temperature and subsequent cooling. The viscosity of an amorphous glass decreases with increasing temperature, that is, the material starts to flow when the temperature applied in the sintering process is significantly higher than the glass transition temperature. The mixture may contain additional substances before the sintering or burning. Additional substances can include a binding agent, a solvent, a surfactant, an additive or any other excipient or a combination of at least two thereof. The components of the amorphous glass are in one embodiment selected from the group consisting of a metal oxide, a metalloid oxide or a mixture thereof. In one embodiment, the amorphous glass includes at least 3 different metal oxides and/or metalloid oxides, in one embodiment at least 5 different metal oxides and/or metalloid oxides, in one embodiment at least 10 different metal oxides and/or metalloid oxides. The metalloid oxide is in one embodiment to be silicon oxide ($SiO_2$). In one embodiment, the metal oxides are selected from the group consisting of barium oxide (BaO), aluminum oxide ($Al_2O_3$), cadmium oxide (CdO), sodium oxide ($Na_2O$), calcium oxide (CaO), strontium oxide (SrO), zinc oxide (ZnO), magnesium oxide (MgO), iron oxide ($Fe_2O_3$), copper oxide (CuO), potassium oxide ($K_2O$), and lead oxide (PbO). In one embodiment, the amorphous glass includes at least 45% by weight silicon oxide, in one embodiment at least 50% by weight silicon oxide, each relative to the composition in the sintered or burned state. In one embodiment, the amorphous glass includes at least 15% by weight barium oxide, in one embodiment at least 25% by weight barium oxide and in one embodiment at least 30% by weight barium oxide, each relative to the composition in the sintered or burned state. In one embodiment, the amorphous glass includes at least 5% by weight aluminum oxide, in one embodiment at least 10% by weight aluminum oxide and in one embodiment at least 15% by weight aluminum oxide, each relative to the composition in the sintered or burned state.

Recrystallizable Glass

According to one embodiment, a recrystallizable glass shall be understood to be a mixture of at least two different metal oxides and/or metalloid oxides that has an amorphous structure in the solid state at room temperature, but forms, at least in part, crystals or crystalline structures after heating to a certain sintering temperature and subsequent cooling. As a result, the recrystallizable glass is stable at high temperatures and is clearly more viscous, that is, more gooey, than comparable non-recrystallizable materials at elevated temperatures. The mixture may contain additional substances before the sintering or burning. Additional substances can include a binding agent, a solvent, a surfactant, an additive or any other excipient or a combination of at least two thereof. The components of the recrystallizable glass are in one embodiment selected from the group consisting of a metal oxide, a metalloid oxide or a mixture thereof. In one embodiment, the recrystallizable glass includes at least 3 different metal oxides and/or metalloid oxides, in one embodiment at least 5 different metal oxides and/or metalloid oxides, in one embodiment at least 10 different metal oxides and/or metalloid oxides. In one embodiment, the metalloid oxides are selected from the group consisting of silicon oxide ($SiO_2$) and boron oxide ($B_2O_3$). In one embodiment, the metal oxides are selected from the group consisting of aluminum oxide ($Al_2O_3$), calcium oxide (CaO), titanium oxide ($TiO_2$), zinc oxide (ZnO), magnesium oxide (MgO), cadmium oxide (CdO), sodium oxide ($Na_2O$), iron oxide ($Fe_2O_3$), zirconium oxide ($ZrO_2$), and chromium oxide ($Cr_2O_3$). In one embodiment, the recrystallizable glass includes at least 25% by weight aluminum oxide, in one embodiment at least 40% by weight aluminum oxide, in one embodiment at least 45% by weight aluminum oxide, and in one embodiment no more than 60% by weight aluminum oxide, each relative to the composition in the sintered or burned state. In one embodiment, the recrystallizable glass includes at least 10% by weight silicon oxide, in one embodiment at least 20% by weight silicon oxide, in one embodiment at least 22% by weight silicon oxide, and in one embodiment no more than 30% by weight silicon oxide, each relative to the composition in the sintered or burned state. In one embodiment, the recrystallizable glass includes at least 10% by weight calcium oxide, in one embodiment at least 18% by weight calcium oxide, in one embodiment at least 20% by weight calcium oxide, and in one embodiment no more than 40% by weight calcium oxide, each relative to the composition in the sintered or burned state. The recrystallizable glass in one embodiment includes at least 1% by weight and no more than 4% by weight of a metal oxide or metalloid oxide selected from the group of boron oxide, titanium oxide, zinc oxide, magnesium oxide, and cadmium oxide or a mixture of at least two thereof.

Cermet

In the scope of one embodiment, "cermet" shall refer to a composite material made of one or more ceramic materials in at least one metallic matrix or a composite material made of one or more metallic materials in at least one ceramic matrix or both. For production of a cermet, for example, a mixture of at least one ceramic powder and at least one metallic powder can be used to which, for example, at least one binding agent can be added. The ceramic powder or powders of the cermet in one embodiment has/have a mean grain size of less than 10 μm, in one embodiment of less than 5 μm, in one embodiment of less than 3 μm. The metallic powder or powders of the cermet in one embodiment has/have a mean grain size of less than 15 μm, in one embodiment of less than 10 μm, in one embodiment of less than 5 μm. For example, the median value or the $D_{50}$ value of the grain size distribution is considered to be the mean grain size in this context. The $D_{50}$ value corresponds to the value at which 50% of the grains of the ceramic powder and/or of the metallic powder are finer than the $D_{50}$ value. In one embodiment cermet includes a high specific conductivity, in one embodiment of at least 1 S/m, in one embodiment of at least 100 S/m, in one embodiment of at least 103 S/m, in one embodiment of at least 104 S/m, in one embodiment of at least 105 S/m, and in one embodiment of at least 106 S/m.

The at least one ceramic component of a cermet according to one embodiment includes one ceramics. The at least one metallic component of a cermet according to one embodiment includes one selected from the group consisting of platinum, iridium, niobium, palladium, iron, stainless steel, a cobalt-chromium alloy, molybdenum, tantalum, tungsten, titanium, cobalt, and zirconium or combination of at least two thereof. In this context, an alloy is a preferred in one embodiment combination. In one embodiment stainless steel is a 316L stainless steel. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content, depending on the selection of materials, should be at least 25% by volume, in one embodiment at least 32% by volume, in one embodiment at least 38% by volume, each relative to the total volume of the cermet.

Firmly Bonded, Sintered Connection

The base body, the conducting element, the adhesion element, and the contact element are connected to each other by a firmly bonded sintered connection. The term, firmly bonded, shall be understood to mean that the two parts to be connected form a unit after being connected and the connection illustrates itself to be at least as stable as at least one of the two parts. As a result, the connected parts may not fracture at the connecting site when exposed to a mechanical load or pressure strain, but rather at a different site of the two connected parts. By this means, it can be ensured that the connection is equally or less porous or gas- or moisture-permeable as/than the parts to be connected. This is also referred to as a hermetically tight connection.

In the scope of the present invention, a sintering, a sintering process or co-sintering shall generally be understood to be a process for the production of materials or workpieces, in which powdered substances, for example, one selected from the group consisting of fine-grained substances, ceramic substances and metallic substances or a combination of at least two thereof, are being heated and thus connected. This process can proceed without applying external pressure onto the substance to be heated or can, for example, proceed at elevated pressure onto the substance to be heated, for example at a pressure of at least 2 bar, in one embodiment higher pressures, for example pressures of at least 10 bar, for example, of at least 100 bar, or even of at least 1000 bar. The process can proceed, for example, fully or partly, at temperatures below the melting temperature of the powdered materials, for example at temperatures of 700° C. to 1400° C. The process can be carried out, for example, fully or partly, in a tool and/or a mold or both such that a forming step can be associated with the sintering process. Aside from the powdered materials, a starting material for the sintering process can include further materials, for example one or more binding agents, but also one or more solvents, surfactants, additives or other excipients or a combination of at least two thereof. The sintering process can proceed in one or more steps, whereby, for example, additional steps can precede the sintering process, for example one or more forming steps and/or one or more debinding steps or both. Accordingly, the sintering and/or the sintering process is equivalent to a burning process The sintering process, for example, of a cermet, can proceed comparable to a sintering process that is commonly used for homogeneous powders. For example, the material can be compacted in the sintering process at high temperature and, if applicable, high pressure such that the cermet is virtually sealed tight or has a closed porosity at most. Usually, cermets are characterized by their particularly high toughness and wear resistance.

Binding Agent

In one embodiment binding agents make a contribution to the obtainment of a composition of suitable stability, suitability for printing, viscosity, and sintering properties. A person skilled in the art is aware of binding agents. All binding agents deemed to be suitable for use in one embodiment by a person skilled in the art can be used as binding agents. Resins are in one embodiment binding agents. Further in one embodiment binding agents include polymeric binding agents, monomeric binding agents, and binding agents made of a combination of polymers and monomers. Polymeric binding agents can be copolymers just as well, whereby at least two monomeric units are present in a single molecule. In one embodiment polymeric binding agents include a functional group in the main chain of the polymer, outside of the main chain or in the main chain and outside of the main chain. In one embodiment binding agents having a functional group in the main chain include polyesters, substituted polyesters, polycarbonates, substituted polycarbonates, polymers with a cyclical group in the main chain, poly-sugars, substituted poly-sugars, polyurethanes, substituted polyurethanes, polyamides, substituted polyamides, phenol resins, substituted phenol resins, copolymers of the monomers of one or more of the polymers specified above, optionally with other co-monomers, or a combination of at least two thereof. In one embodiment polymers having a cyclical group in the main chain include polyvinylbutylates (PVB) and the derivatives thereof, and polyterpineol and the derivatives thereof, or mixtures thereof. In one embodiment poly-sugars include cellulose and alkyl derivatives thereof, in one embodiment methylcellulose, ethylcellulose, propylcellulose, butylcellulose and the derivatives thereof, and mixtures of at least two thereof. In one embodiment polymers having a functional group outside their main chain are those with an amide group, with an acid group and/or an ester group (also called acrylic resins) or polymers having a combination of the aforementioned functional groups. In one embodiment polymers with an amide group outside of the main chain include polyvinyl pyrrolidone (PVP) and the derivatives thereof. In one embodiment polymers with an acid group and/or an ester group outside of the main chain include polyacrylic acid and the derivatives thereof, polymethacrylate (PMA) and the derivatives thereof, and polymethylmethacrylate (PMMA) and the derivatives thereof, or combinations of at least two thereof. In one embodiment monomeric binding agents include ethylene glycol-based monomers, terpineol resins, and resin derivatives, or a combination of at least two thereof. In one embodiment ethylene glycol-based monomeric binding agents have an ether group, an ester group or both. In this context, in one embodiment ether groups include methyl, ethyl, propyl, butyl, pentyl, hexyl, and higher alkylether groups. In one embodiment ester groups include acetates and the alkyl derivatives thereof, in one embodiment ethylene glycol-monobutyl ether-monoacetate or a mixture of the aforementioned. In one embodiment binding agents include alkylcellulose, in one embodiment ethylcellulose and the derivatives thereof, and mixtures thereof that include other binding agents selected from amongst the aforementioned or others.

Biocompatible Material

The materials that are used according to one embodiment are to be biocompatible materials. Biocompatible materials are selected from the group consisting of biotolerant, bioinert and bioactive or any combination of at least two thereof.

Embodiments are illustrated in the following by means of drawings and exemplary embodiments, without the drawings and exemplary embodiments limiting the embodiments in any way or manner. Unless specified otherwise, the drawings are not true to scale.

FIG. 1 illustrates a cross-section of an electrical contacting device (100) according to a first embodiment. The contacting device is well-suited, for example, as an electrical bushing from an internal part of a housing of a medical implantable device to an external part, that is, to the body fluid side. The contacting device (100) includes an electrically insulating base body (103) having a first surface (105) and a second surface (106). The base body consists of highly pure aluminum oxide. An electrically conductive conducting element (104) extends from the first surface (105) to the second surface (106) of the base body (103). The conducting element (104) includes a cermet made of sintered platinum particles and aluminum oxide particles, whereby the platinum fraction is approximately 40% by volume and the aluminum oxide fraction is approximately 60% by volume, relative to the cermet in the sintered state. The cermet of the conducting element (104) is connected to the base body (103) through a firmly bonded, sintered connection. The contacting device (100) further includes an adhesion element (101) that is connected to the base body (103), the conducting element (104) as well as a contact element (102) through a firmly bonded, sintered connection. The adhesion element (101) includes a cermet made of platinum particles and aluminum oxide particles. The platinum particles serve mainly for electrically connecting the conducting element (104) and the contact element (102), but also serve for the adhesion to the conducting element (104) as well as to the contact element (102) by means of diffusion of the metal particles of the individual elements in the course of the sintering process. The contact element (102) consists of platinum. The aluminum oxide particles act as an adhesion promoter with respect to the base body (103) and thus provide for a strongly adhesive connection between the adhesion element (101) and the base body (103). The contact element (102) is connected to the adhesion element (101) through a firmly bonded, sintered connection, and the same is true of the connection between the adhesion element (102) and the first surface (105) of the base body (103) and the surface of the conducting element (104). In the example illustrated, the adhesion element (101) extends over a majority of the first surface (105) of the base body (103) such that the contact element (102) can be placed at a position that is offset with respect to an end of the conducting element (104). This allows the contacting to be designed variably through the aid of an electrically conductive structure (not illustrated) on the contact element (102), independent of the position of the conducting element (104) in the base body (103) of the contacting device (100).

Figure 2A:
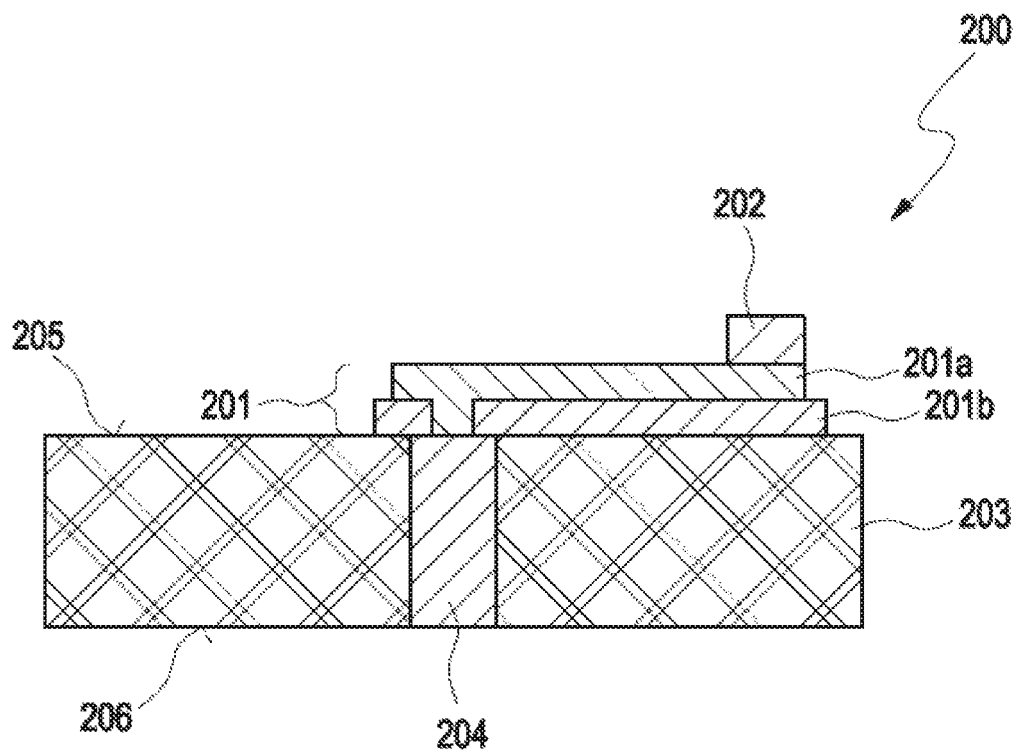
FIG. 2a illustrates a cross-sectional view of another embodiment of the contacting device according to one embodiment.

FIG. 2a illustrates a cross-section of an electrical contacting device (200) according to another embodiment. The contacting device is well-suited, for example, as an electrical bushing from an internal part of a housing of a medical implantable device to an external part, that is, to the body fluid side. The contacting device (200) includes an electrically insulating base body (203) having a first surface (205) and a second surface (206). The base body consists of highly pure aluminum oxide. An electrically conductive conducting element (204) extends from the first surface (205) to the second surface (206) of the base body (203). The conducting element (204) includes a cermet made of sintered platinum particles and aluminum oxide particles, whereby the platinum fraction is approximately 40% by volume and the aluminum oxide fraction is approximately 60% by volume, relative to the cermet in the sintered state. The cermet of the conducting element (204) is connected to the base body (203) through a firmly bonded, sintered connection. The contacting device (200) includes an adhesion element (201) consisting of a first layer (201a) and a second layer (201b). The first layer (201a) of the adhesion element extends through the second layer (201b) to the conducting element (204). The first layer (201a) includes a cermet made of sintered platinum particles and aluminum oxide particles. The platinum particles mainly serve for producing an electrical connection between the conducting element (204) and a contact element (202). The platinum particles of the cermet of the first layer (201a) of the adhesion element (201) improve the adhesion to the contact element (202) and to the conducting element (204) through diffusion of the metal particles of the individual elements in the course of the sintering process. The contact element (202) consists of platinum. The second layer (201b) of the adhesion element (201) includes a dielectric material as adhesion promoter. The dielectric material provides for a strongly adhesive connection to the base body (203) made of aluminum oxide and the first layer (201a), since the first layer includes a fraction of aluminum oxide. In the example illustrated, the dielectric material that is used is a recrystallizable glass made of 48% by weight aluminum oxide ($Al_2O_3$), 23% by weight silicon oxide ($SiO_2$), 21% by weight calcium oxide (CaO), 4% by weight boron oxide ($B_2O_3$), 1% by weight each of zinc oxide (ZnO), magnesium oxide (MgO), and cadmium oxide (CdO) as well as traces of sodium, iron, zirconium and chromium oxides, relative to the sintered state of the recrystallizable glass. In this context, the second layer (201b) includes a hole as a recess through which the first layer (201a) extends to the conducting element (204). The recess, that is, the hole of the second layer, can be provided, for example, as a circular hole. All connections between the layers of the adhesion element (201a, 201b), the contact element (202), the conducting element (204), and the first surface (205) of the base body (203) illustrated in FIG. 2a are firmly bonded, sintered connections. In this context, the second layer (201b) of the adhesion element (202) is connected to both the first surface (205) of the base body (203) and to the surface of the conducting element (204). In the example illustrated, the adhesion element (201) extends over a majority of the first surface (205) of the base body (203) such that the contact element (202) can be placed at a position that is offset with respect to an end of the conducting element (204). This allows the contacting to be designed variably through the aid of an electrically conductive structure (not illustrated) on the contact element (202), independent of the position of the conducting element (204) in the base body (203) of the contacting device (200).

Figure 2B:
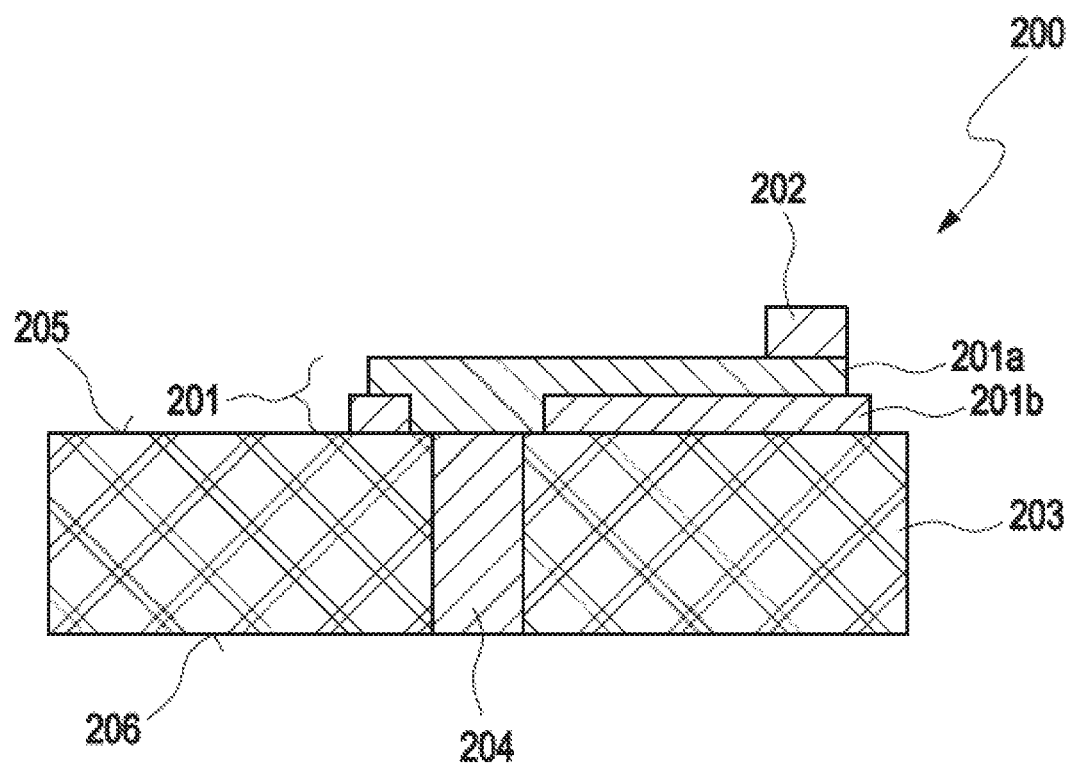
FIG. 2b illustrates a cross-sectional view of another embodiment of the contacting device according to one embodiment.

FIG. 2b illustrates a cross-section of an electrical contacting device (200) according to yet another embodiment. In this context, the contacting device (200) of FIG. 2b differs from the contacting device (200) of FIG. 2a in that the second layer of the adhesion element (201b) is not connected to the surface of the conducting element (204). The second layer of the adhesion element is only connected to the first surface (205) of the base body (203) and to the first layer (201a) of the adhesion element (201). The second layer (201b) includes a hole as recess through which the second layer (201a) of the adhesion element extends to the contact element and to the first surface (205) of the base body (203), that is, the second layer forms a firmly bonded connection to the conducting element (204) and to the base body (205). The recess, that is, the hole of the second layer, can be provided, for example, as a circular hole.

Figure 3:
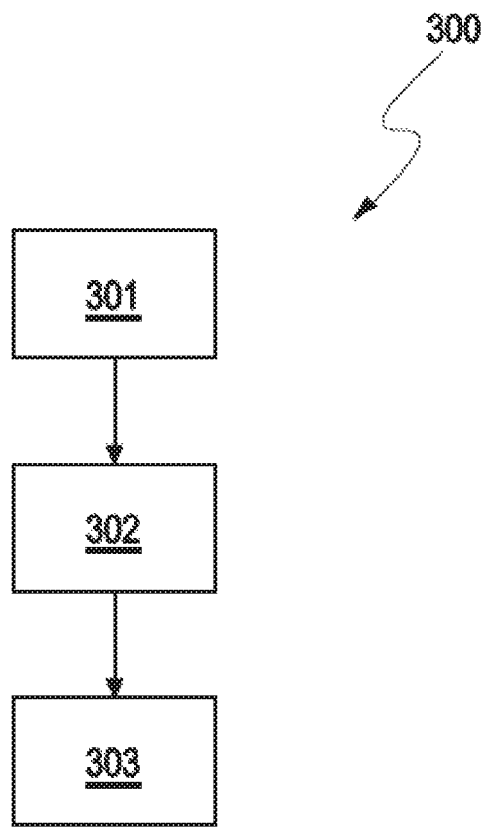
FIG. 3 illustrates a flow diagram of the method according to one embodiment.

FIG. 3 illustrates a schematic workflow of the method according to one embodiment (300) for the production of a contacting device according to one embodiment. In this context, an electrically insulating base body with a first and a second surface is provided in a first step (301), whereby the base body includes a ceramics, and an electrically conductive conducting element that is integrated into the base body and extends from the first surface of the base body through the base body, whereby the conducting element includes a cermet and is connected in firmly bonded manner to the ceramics of the base body through a sintered connection. The base body with the conducting element is characterized by its multi-layered design, that is, the buildup of the base body with conducting element takes place by laminating aluminum oxide layers that are provided with orifices and filling the orifices with a cermet paste, which is subsequently being co-sintered with the aluminum oxide. The adhesion element and the contact element are applied after co-sintering of the laminate. Accordingly, an adhesion element precursor is applied in a second step (302). The adhesion element precursor includes one or two pastes, depending on the layer structure. Sintering the adhesion element precursor in a sintering step 1 generates a firmly bonded connection between the adhesion element and the base body and, optionally, the surface of the conducting element. In this context, sintering step 1 can include two separate sintering steps in case the adhesion element includes more than one layer. In this case, the second layer of the adhesion element precursor is applied and sintered first before the first layer of the adhesion element precursor is applied and sintered. The contact element is generated in a further step (303) by applying a contact element precursor and sintering it in a sintering step 2, whereby an electrical connection between the contact element and the conducting element as well as a firmly bonded connection between the contact element and the adhesion element are generated.

The following exemplary embodiments illustrate the production of an electrical contacting device in more detail.

Preparation of Ceramic Green Body Foils

Ceramic green body films were used as ceramics precursor for the insulating base body. For this purpose, 99% by weight pure $Al_2O_3$ foils (Maryland Ceramic & Steatite Company Inc.) with a thickness of 400 µm were used. Samples of the green body foils were cut into squares of 100 mm×100 mm. Approximately circular holes with a diameter of 400 µm were punched into the foil samples using a mechanical punching tool (for 400 µm diameters) in an automatic punch. At least 4 foil samples were prepared by this means.

Filling

The holes prepared as described above were filled with cermet paste using a printing stencil and an EKRA Microtronic II printer (model M2H).

For the cermet paste, platinum powder and $Al_2O_3$ powder were mixed with an organic binding agent and homogenized in a 3-roller mill. The viscosities of the pastes thus obtained were in the range of 250 to 500 Pa*s (measured using a Haake Rheostress 6000 rheometer at 25° C.) and the fineness of grind (FoG) was less than 20 μm. The rheology of the pastes was suitable for subsequent stencil printing.

The thickness of the stencil was 100 μm. The orifices of the stencil had the same dimensions and positions as the holes, which had been punched into the green body foil as described above. The printing parameters were 50 N squeegee pressure, squeegee forward rate 25 mm/s, squeegee backward rate 25 mm/s and snap off of 0.0 mm. The squeegee circle was adjusted appropriately such that paste material was introduced both during the forward motion and the backward motion.

Ten minutes after the samples were filled, the samples were introduced into a HHG-2 dryer (BTU International Inc.) and dried in it for 10 minutes at 75° C.

Additional filling steps with the cermet paste were carried out to completely fill the hole of the foil. A total of 1 to 5 foil samples were completely filled with the cermet paste by repeating the filling step above.

Laminating the Green Body Foils

A total of 4 layers of green body foil with the holes filled as described above were stacked and pressed isostatically in one step using a metal aligning tool.

Sintering

The laminate of green body foils obtained as described above was burned in a high-temperature chamber furnace with a chamber size of 200 mm×250 mm×200 mm in order to sinter the individual layers and cermet fillings. The sintering process took place at normal atmospheric conditions. The temperature was slowly increased from 25 to 450° C. Then the temperature was kept constant at 450° C. for 1 h in order to expel the organic components from the green body laminate. Subsequently, the temperature was quickly increased to a maximum temperature in the range of 1510 to 1560° C. and then maintained in this range for a holding time in the range of 1 to 2 hours. Then the temperature was lowered to room temperature at a cooling rate of 500° C./h or at the natural cooling rate, which was slower.

Sintered molded bodies with a volume fraction of 40% by volume to 45% by volume platinum in the cermet were obtained.

After-Treatment

After the burning process, the samples were sanded, and cut to the desired dimensions using a laser.

The sintered samples were sanded on both sides to attain a thickness of 1.0 to 1.1 mm. Individual areas were separated from the sanded samples using a laser cutting process. Areas, which each contained 5 double rows of cermet conducting elements per sample, were obtained.

Generating the Adhesion Element and Contact Element on the Samples

EXAMPLE 1

A sample produced as described above was used as substrate. A cermet paste including platinum powder and $Al_2O_3$ powder and an organic binding agent was printed onto the surface of the base body and of the conducting element using a screen printing procedure (mesh width 200 mesh/30 μm layer thickness of the emulsion). The sample was sintered at 1450° C. (retention time: 2 h) at normal atmospheric conditions in a high-temperature chamber furnace. An additional layer of a glass- and ceramics-free platinum paste, consisting only of platinum particles and an organic vehicle, was printed onto the sintered adhesion element using a screen printing procedure (mess width 200 mesh/30 μm layer thickness of the emulsion). The sample was sintered again at 1150° C. or 1300° C. for a retention time of 40 min.

EXAMPLE 2

A sample produced as described above was used as substrate. A dielectric paste including a recrystallizing glass and a binding agent was printed onto the surface of the base body and of the conducting element using a screen printing procedure (mess width 200 mesh/30 μm layer thickness of the emulsion), whereby part of the surface of the conducting element was not exposed to printing, that is, was kept unoccupied. The sample was sintered at 850° C. for 1 h (retention time at 850° C.: 10 min) at normal atmospheric conditions in a high-temperature chamber furnace. A cermet paste including a platinum powder and an $Al_2O_3$ powder and an organic binding agent based on ethylcellulose was printed onto the surface of the layer of recrystallizable glass that was applied first using a screen printing procedure (mesh width 200 mesh/30 μm layer thickness of the emulsion). The sample was sintered at 1550° C. (retention time: 0.5 h) at normal atmospheric conditions in a high-temperature chamber furnace. An additional layer of a glass- and ceramics-free platinum paste, consisting only of platinum particles and an organic vehicle, was printed onto the sintered adhesion element using a screen printing procedure (mess width 200 mesh/30 μm layer thickness of the emulsion), whereby the previously unoccupied region of the conducting element was included in the printing. The sample was sintered again at 1150° C. or 1300° C. (retention time at 1150° C. or 1300° C.: 40 min).

Test Methods

Adhesion

The adhesion of the sintered layers (adhesion element and contact element) was tested with the so-called tape pull test. For this purpose, a piece of Tesa® tape was taped to the areas exposed to the printing according to the procedure illustrated above. To make sure that the tape adheres fully to the area exposed to the printing, the film was firmly pushed on using a piece of rubber. Then the tape was removed again in a slow and constant motion (pull off rate approx. 1 second per inch). The sample and the tape was subsequently assessed by visual inspection. In none of the samples thus produced, any part of the printed area stuck to the tape.

As an alternative to this test, the adhesion of the sintered layers in the sample was tested in the so-called scratch test test. For this purpose, the tip of stainless steel tweezers was scraped over the areas exposed to printing and the sample was subsequently assessed by visual inspection. None of the samples thus produced illustrated any signs that any part of the area exposed to printing was removed by the work of the tweezers.

Solderability

The solderability of the printed layers, for example, with regard to the contact element, describes the ability of the corresponding printed layer to be wetted by a solder. Only if wetting is observed, it is possible to solder a wire to the contact element under using a soldered connection under standard conditions. To test the solderability, one corner of the sample was immersed for 5 seconds in a vessel containing solder (type SAC305 made by AIM) liquefied at 255° C. such that an area of the ceramics of the base body, an area of the adhesion element (platinum-cermet or recrystallizable glass), and an area of the contact element (platinum) contacted the solder. It was observed, as desired, that only the contact element made of platinum was wetted by the solder.

The platinum-cermet and the aluminum oxide of the base body illustrated no signs of being wetted by the solder.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. An electrical contacting device for a medical implantable device, comprising:
   an electrically insulating base body with a first and a second surface;
   wherein the base body includes a ceramics;
   an electrically conductive conducting element that extends, at least in part, from the first surface of the base body through the base body;
   wherein the conducting element includes a cermet and is connected to the ceramics of the base body in firmly bonded manner through a sintered connection;
   a contact element including a metal, wherein the contact element is connected via an adhesion element to the conducting element in an electrically conductive manner and can be connected to an electrically conductive structure;
   wherein the adhesion element is connected to the contact element in a firmly bonded manner; and
   wherein the adhesion element includes an adhesion promoter in order to form a firmly bonded connection at least to the first surface of the base body.

2. The electrical contacting device according to claim 1, wherein the adhesion element comprises a first layer, wherein the first layer includes a metal.

3. The electrical contacting device according to claim 1, wherein the adhesion promoter includes a ceramics, an amorphous glass, a recrystallizable glass or a combination of at least two thereof.

4. The electrical contacting device according to claim 3, wherein the adhesion element includes a cermet.

5. The electrical contacting device according to claim 3, wherein the amorphous glass includes at least 45% by weight silicon oxide ($SiO_2$).

6. The electrical contacting device according to claim 3, wherein the recrystallizable glass includes at least 25% by weight aluminum oxide ($Al_2O_3$) and no more than 30% by weight silicon oxide ($SiO_2$).

7. The electrical contacting device according to claim 1, wherein the adhesion element and the base body form an oxidic mixed crystal layer.

8. The electrical contacting device according to claim 1, wherein the conducting element extends from the first surface of the base body through the base body to the second surface of the base body.

9. A medical implantable device, comprising a contacting device according to claim 1.

10. A cardiac pacemaker, defibrillator, neurostimulator, cochlear implant, glucose monitor or implantable infusion pump comprising an electrical contacting device according to claim 1.

11. The use of an electrical contacting device according to claim 1.

12. An electrical contacting device for a medical implantable device, comprising:
   an electrically insulating base body with a first and a second surface;
   wherein the base body includes a ceramics;
   an electrically conductive conducting element that extends, at least in part, from the first surface of the base body through the base body;
   wherein the conducting element includes a cermet and is connected to the ceramics of the base body in firmly bonded manner through a sintered connection;
   a contact element including a metal, wherein the contact element is connected to the conducting element in electrically conductive manner and can be connected to an electrically conductive structure;
   wherein the contacting device comprises an adhesion element, wherein the adhesion element is connected to the contact element in firmly bonded manner;
   wherein the adhesion element includes an adhesion promoter in order to form a firmly bonded connection at least to the first surface of the base body; and
   wherein the adhesion element comprises a first layer, wherein the first layer includes a metal and extends through a second layer to the conducting element, wherein the second layer includes a dielectric material and is connected in firmly bonded manner to at least the first layer and the first surface of the base body.

13. A method for the production of an electrical contacting device for a medical implantable device, wherein the method comprises:
   a. providing an electrically insulating base body having a first and a second surface, wherein the base body comprises a ceramics, and wherein the base body includes an electrically conductive conducting element that extends, at least in part, from the first surface of the base body through the base body, wherein the conducting element includes a cermet and is connected in firmly bonded manner to the ceramics of the base body through a sintered connection;
   b. generating an adhesion element comprising an adhesion promoter on the base body through a sintering step 1 from an adhesion element precursor while forming a firmly bonded connection between the adhesion element and the first surface of the base body and between the adhesion element and the conducting element; and
   c. generating a contact element including a metal on the adhesion element through a sintering step 2 from a contact element precursor to form a firmly bonded connection between the contact element and the adhesion element and form an electrical connection between the contact element and the conducting element via the adhesion element.

14. The method according to claim 13, wherein the adhesion element precursor includes at least one paste 1, wherein paste 1 includes at least a metal, an adhesion promoter, and a binding agent.

15. The method according to claim 14, wherein, in sintering step 1, paste 1 is being applied to the base body and sintered, wherein the adhesion element is formed while forming a firmly bonded connection to the conducting element and to the first surface of the base body.

16. The method according to claim 13, wherein the adhesion element precursor includes a paste 2, wherein paste 2 includes at least an adhesion promoter and a binding agent.

17. The method according to claim 16, wherein, in sintering step 1, paste 2 is initially applied appropriately to the base body and sintered such that at least a part of an exposed surface of the conducting element is not covered by paste 2, and subsequently paste 1 is applied onto the sintered paste 2 and sintered, wherein the adhesion element is formed while forming a firmly bonded connection to the conducting element and to the first surface of the base body.

18. An electrical contacting device for a medical implantable device, obtainable through a method according to claim 13.

19. An electrical contacting device for an implantable medical device including an electrically insulating base body with a first and a second surface and including a conductive element that extends through the base body between the first and second surfaces, wherein the base body comprises ceramics and the conducting element includes a cermet, the conducting element bonded to the base body with a sintered connection, the electrical contacting device including:
 an adhesion element disposed on the first surface of the base body and the conductive element, the adhesion element including an adhesion promoter to form a bonded connection to the first surface and the conductive element; and
 a contact element including a metal, the contact element, the contact element bonded to the adhesion element in an electrically conductive fashion and electrically connected to the conductive element via the adhesion element, the contact element connectable to an electrically conductive structure.

20. The electrical contacting device of claim 19, wherein the adhesion element having a sintered connection with the based body, the conductive element, and the contact element.

21. The electrical contacting device of claim 20, the adhesion element including:

a second layer bonded to at least a portion of the first surface of the base body and includes an opening through which the conductive element is exposed; and
 a first layer bonded to the second layer, such that the second layer is disposed between the first layer and the base body, the first layer extending through the opening to electrically connect to the conductive element, wherein the contact element is electrically connected to the first layer such that the conductive element is electrically connected to the contact element via the first layer.

22. The electrical contacting device of claim 21, wherein:
 the first layer comprises a cermet including platinum particles and aluminum oxide particles, the platinum particles to serve as an adhesion promoter to bond the adhesion element to the conductive element and to the contact element and to electrically connect the conductive element to the contact element; and
 the second layer comprises a dielectric material to serve as an adhesion promoter to form a connection with the base body.

23. The electrical contacting device of claim 19, the adhesion element comprising cermet including platinum particles and aluminum oxide particles, the platinum particles to serve as an adhesion promoter to bond the adhesion element to the conductive element and to the contact element and to electrically connect the conductive element to the contact element, and the aluminum oxide particles to serve as an adhesion promoter to form a connection with the base body.

* * * * *